(12) United States Patent
Yamaguchi et al.

(10) Patent No.: US 6,379,688 B2
(45) Date of Patent: Apr. 30, 2002

(54) PRESERVATIVE FOR EMULSION AND EMULSION CONTAINING SAME

(75) Inventors: Masazumi Yamaguchi; Masayo Yamaguchi; Katsuhiro Inada, all of Kobe (JP)

(73) Assignee: Senju Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/028,311

(22) Filed: Feb. 24, 1998

(30) Foreign Application Priority Data

Feb. 28, 1997 (JP) .............................. 9-046548

(51) Int. Cl.⁷ .............................. A01N 25/04
(52) U.S. Cl. ..................... 424/406; 424/405; 424/459; 514/557; 514/939
(58) Field of Search ................ 510/324, 417; 424/405, 406, 659; 514/937, 557

(56) References Cited

U.S. PATENT DOCUMENTS

| | | | |
|---|---|---|---|
| 3,906,108 A | 9/1975 | Felty | 424/318 |
| 3,911,107 A | 10/1975 | Krezanoski | 424/78 |
| 4,031,209 A | 6/1977 | Krezanoski | 424/150 |
| 4,188,373 A | 2/1980 | Krezanoski | 424/78 |

FOREIGN PATENT DOCUMENTS

| | | |
|---|---|---|
| EP | 0 572 190 A1 | 12/1993 |
| EP | 0 610 502 A1 | 8/1994 |
| EP | 0 642 789 A1 | 3/1995 |

OTHER PUBLICATIONS

Database WPIL on Questel, Week 8917, London: Derwent Publication Ltd., AN 89–125493, (Santen Seiyaku K.K.), Abstract.

Database WPIL on Questel, Week 9631, London: Derwent Publications Ltd., AN 96–306468, (EISAI Co., Ltd.), Abstract.

Database WPIL on Questel, Week 9640, London: Derwent Publications Ltd., AN 96–397204, (Ikeda Mohando Co., Ltd.), Abstract.

Database WPIL on Questel, Week 9518, London: Derwent Publications Ltd., AN 95–136791, (Kyowa Hakko Kogyo K.K.), Abstract.

Database WPIL on Questel, Week 9343, London: Derwent Publications Ltd., AN 93–342980, (Novo Nordisk As), Abstract.

Database WPIL on Questel, Week 7701, London: Derwent Publications Ltd., AN 77–00230y, (Flow Pharmaceutical), Abstract. See also AB and AC.

Primary Examiner—Neil Levy
(74) Attorney, Agent, or Firm—Wenderoth, Lind & Ponack, L.L.P.

(57) ABSTRACT

A preservative for emulsion, comprising sorbic acid or a pharmaceutically acceptable salt thereof, and, where necessary, sodium edetate and boric acid; an emulsion comprising sorbic acid or a pharmaceutically acceptable salt thereof, and, where necessary, sodium edetate and boric acid; an emulsion comprising the preservative; a method for preserving an emulsion comprising adding sorbic acid or a pharmaceutically acceptable salt thereof, and, where necessary, sodium edetate and boric acid, at a concentration pharmaceutically acceptable and effective for the preservation of the emulsion; use of sorbic acid or a pharmaceutically acceptable salt thereof for the production of an emulsion or preservative for emulsion; and the use comprising adding, where necessary, sodium edetate and boric acid. The sorbic acid or a pharmaceutically acceptable salt thereof and emulsions comprising them can impart superior preservation capability to emulsions, such as water in oil (O/W) type emulsions, so that an emulsion having high preservation property and less side effects is provided. The addition of sodium edetate and boric acid provides an emulsion having a high pH with superior preservation property even at low concentration of the preservative.

6 Claims, No Drawings

PRESERVATIVE FOR EMULSION AND EMULSION CONTAINING SAME

TECHNICAL FIELD OF THE INVENTION

The present invention relates to a preservative for emulsion, said preservative containing sorbic acid or a pharmaceutically acceptable salt thereof and exhibiting superior preservation effect at a low concentration, and to an emulsion containing said compound or a preservative for emulsion containing said compound, along with an active ingredient, which can be administered safely to humans. The present invention further relates to a method for preserving an emulsion, which comprises adding a sorbic acid or a pharmaceutically acceptable salt thereof to said emulsion. The present invention moreover relates to use of sorbic acid or a pharmaceutically acceptable salt thereof for the preservation of an emulsion, as well as to use of said compound for the production of an emulsion and a preservative for emulsion.

BACKGROUND OF THE INVENTION

When formulating a drug into an eye drop, a nasal drop or an ear drop, a preservative is added to eliminate a secondary contamination with microorganisms present in the air, lacrimal fluid, meatus nasi, external auditory meatus and the like. The same applies to an emulsion. Thus, paraoxybenzoate, benzalkonium chloride and the like are generally added as a preservative when formulating a drug into an emulsion. However, such conventional preservatives cannot provide an emulsion, particularly an oil in water type (o/w type) emulsion, with a sufficient preservation effect. In addition, when a dispersion medium has a relatively high pH, microorganisms tend to proliferate, further reducing the preservation effect. Nevertheless, an increased amount of a preservative for a higher preservation effect is associated with possible side effects such as greater irritation etc. to the living body due to the high concentration preservative.

Thus, there is a dilemma as to whether to add a preservative at a high concentration to increase preservation effect or limit the amount to be added to avoid side effects caused by the high concentration preservative, when formulating a drug into an emulsion. Therefore, development of a preservative capable of imparting a superior preservation capability to an emulsion at a low concentration has been demanded.

SUMMARY OF THE INVENTION

It is therefore an object of the present invention to provide a compound capable of imparting a superior preservation capability to an emulsion even when added at a low concentration, particularly an oil in water type (o/w type) emulsion, among others, an oil in water type emulsion comprising a dispersion medium having a high pH, and a preservative for emulsion containing said compound.

Another object of the present invention is to provide an emulsion containing said compound or said preservative, which has superior preservation effect and which can be administered safely to humans, particularly an emulsion for an eye drop, a nasal drop and an ear drop.

As a result of intensive studies in an attempt to solve the above-mentioned problems, it has now been found that the addition of sorbic acid or a pharmaceutically acceptable salt thereof to an emulsion leads to a high preservation effect of the emulsion, even when the concentration thereof is low. It has also been found that, when the emulsion has a high pH, the addition, at a low concentration, of sodium edetate and boric acid along with the sorbic acid or a pharmaceutically acceptable salt thereof also leads to a more superior preservation effect of the emulsion.

In one aspect, the present invention provides a preservative for emulsion which contains sorbic acid or a pharmaceutically acceptable salt thereof, particularly such preservative for emulsion which contains said compound at a concentration of 0.001–5 w/v %, preferably 0.01–1 w/v %; further, the above-mentioned preservative for emulsion which contains, in addition to said compound, sodium edetate and boric acid, particularly said preservative for emulsion which contains sodium edetate at a concentration of 0.001–0.2 w/v %, preferably 0.005–0.1 w/v %, and boric acid at a concentration of 0.001–10 w/v %, preferably 0.01–5 w/v %; and further, the above-mentioned preservative for emulsion which is in the dosage form of an eye drop, a nasal drop or an ear drop.

In another aspect, the present invention provides an emulsion which contains sorbic acid or a pharmaceutically acceptable salt thereof, or a preservative for emulsion containing said compound, together with an active ingredient and a pharmaceutically acceptable carrier, particularly, the above-mentioned emulsion containing sorbic acid or a pharmaceutically acceptable salt thereof at a concentration of 0.001–5 w/v %, particularly 0.01–1 w/v %; further, an emulsion comprising a preservative containing sorbic acid or a pharmaceutically acceptable salt thereof, sodium edetate and boric acid, together with an active ingredient and a pharmaceutically acceptable carrier, or an emulsion comprising a preservative containing sorbic acid or a pharmaceutically acceptable salt thereof, sodium edetate and boric acid, together with an active ingredient and a pharmaceutically acceptable carrier; particularly, the above-mentioned emulsion containing sorbic acid or a pharmaceutically acceptable salt thereof at a concentration of 0.001–5 w/v %, preferably 0.01–1 w/v %, sodium edetate at a concentration of 0.001–0.2 w/v %, preferably 0.005–0.1 w/v %, and boric acid at a concentration of 0.001–10 w/v %, particularly 0.01–5 w/v %; and further, the above-mentioned emulsion which is in the dosage form of an eye drop, a nasal drop or an ear drop.

In another aspect, the present invention provides a commercial package containing a preservative for emulsion containing sorbic acid or a pharmaceutically acceptable salt thereof, and, where necessary, sodium edetate and boric acid, along with a pharmaceutically acceptable carrier, and a package insert stating that said preservative is useful for the preservation of the emulsion; and a commercial package comprising either an emulsion containing sorbic acid or a pharmaceutically acceptable salt thereof, and, where necessary, sodium edetate and boric acid, together with an active ingredient and a pharmaceutically acceptable carrier, or a preservative for emulsion containing sorbic acid or a pharmaceutically acceptable salt thereof, and, where necessary, sodium edetate and boric acid, together with an active ingredient and a pharmaceutically acceptable carrier, and a package insert stating that sorbic acid, a pharmaceutically acceptable salt thereof and the combination of said compound, sodium edetate and boric acid are useful for the preservation of an emulsion.

Also, the present invention provides a preservation method of an emulsion, which comprises adding sorbic acid or a pharmaceutically acceptable salt thereof to an emulsion at a concentration pharmaceutically acceptable and effective for the preservation of the emulsion, particularly, sorbic acid or a pharmaceutically acceptable salt thereof at a concentration of 0.001–5 w/v %, preferably 0.01–1 w/v %. The present invention further provides a preservation method of an emulsion, which comprises adding sorbic acid or a pharmaceutically acceptable salt thereof, sodium edetate and boric acid to an emulsion at concentrations pharmaceutically acceptable and effective for the preservation of the emulsion, particularly, sorbic acid or a pharmaceutically acceptable salt thereof at a concentration of 0.001–5 w/v %, preferably 0.01–1 w/v %, sodium edetate at a concentration of 0.001–0.2 w/v %, preferably 0.005–0.1 w/v %, and boric acid at a concentration of 0.001–10 w/v %, preferably, 0.01–5 w/v %. The present invention is a preservation method of the above-mentioned emulsion in the dosage form of an eye drop, a nasal drop or an ear drop.

The present invention also provides use of sorbic acid or a pharmaceutically acceptable salt thereof for the preservation of an emulsion, particularly, use comprising adding sorbic acid or a pharmaceutically acceptable salt thereof at a concentration of 0.001–5 w/v %, particularly 0.01–1 w/v %. Further, the present invention provides the use of sorbic acid or a pharmaceutically acceptable salt thereof, sodium edetate and boric acid for the preservation of an emulsion, particularly, the use comprising adding sorbic acid or a pharmaceutically acceptable salt thereof at a concentration of 0.001–5 w/v %, particularly 0.01–1 w/v %, sodium edetate at a concentration of 0.001–0.2 w/v %, particularly 0.005–0.1 w/v %, and boric acid at a concentration of 0.001–10 w/v %, particularly 0.01–5 w/v %. The present invention provides use wherein said emulsion is in the dosage form of an eye drop, a nasal drop or an ear drop.

In a further aspect, the present invention provides use for the production of an emulsion or a preservative for an emulsion, which comprises adding sorbic acid or a pharmaceutically acceptable salt thereof, particularly sorbic acid or a pharmaceutically acceptable salt thereof at a concentration of 0.001–5 w/v %, preferably 0.01–1 w/v %. Further, the present invention provides the above-mentioned use for the production of an emulsion or a preservative for emulsion, which comprises adding sorbic acid or a pharmaceutically acceptable salt thereof, sodium edetate and boric acid, particularly sorbic acid or a pharmaceutically acceptable salt thereof at a concentration of 0.001–5 w/v %, preferably 0.01–1 w/v %, sodium edetate at a concentration of 0.001–0.2 w/v %, preferably 0.005–0.1 w/v %, and boric acid at a concentration of 0.001–10 w/v %, preferably 0.01–5 w/v %. The present invention provides the above-mentioned use wherein said emulsion is in the dosage form of an eye drop, a nasal drop or an ear drop.

DETAILED DESCRIPTION OF THE INVENTION

The inventive preservative for emulsion contains sorbic acid or a pharmaceutically acceptable salt thereof. The pharmaceutically acceptable salt of the sorbic acid to be used in the present invention is exemplified by alkali metal salts such as sodium and potassium, alkaline earth metal salts such as calcium and magnesium, and the like.

When the preservative for emulsion of the present invention is added to an emulsion having a pH of not less than 6.0, it is preferable that said preservative for emulsion contain sodium edetate and boric acid, in addition to sorbic acid or a pharmaceutically acceptable salt thereof.

The concentration of sorbic acid or a pharmaceutically acceptable salt thereof to be contained in the preservative for emulsion is 0.001–5 w/v %, preferably 0.01–1 w/v %. When sodium edetate and boric acid are further contained, the concentration of sodium edetate is 0.001–0.2 w/v %, preferably 0.005–0.1 w/v %, and that of boric acid is 0.001–10 w/v %, preferably 0.01–5 w/v %.

The inventive preservative for emulsion may contain, besides sorbic acid or a pharmaceutically acceptable salt thereof, emulsifiers such as polysorbate 80 and polyoxyethylene hydrogenated castor oil 60, buffering agents such as sodium acetate and disodium hydrogenphosphate, isotonizing agents such as sodium chloride and glycerin, and the like.

The inventive preservative for emulsion can be prepared by a known method. For example, sorbic acid or a pharmaceutically acceptable salt thereof is dissolved in sterile purified water or an aqueous solvent. In this solution is dissolved, as necessary, sodium edetate and boric acid, and the above-mentioned additives are added on demand.

The inventive preservative for emulsion is not subject to any particular limitation as long as it can be added to any emulsion. When it is used for an oil in water (o/w) type emulsion, said preservative becomes a dispersion medium, and when it is used for a water in oil (w/o) type emulsion, said preservative becomes a disperse phase.

The inventive preservative for emulsion can achieve superior preservation effect in various types of emulsions such as oil in water (o/w) type emulsion, even when added at a low concentration. By adding the inventive preservative for emulsion to an emulsion, therefore, the emulsion shows high preservation effect and extremely less side effects, as a result of the low concentration of the preservative.

The emulsion of the present invention is not particularly limited as to use thereof as long as it contains sorbic acid or a pharmaceutically acceptable salt thereof, or the above-mentioned preservative for emulsion, together with the active ingredient. For example, it is a therapeutically useful emulsion. The drug to be the active ingredient is not particularly limited, and is exemplified by various drugs such as steroidal anti-inflammatory agent, non-steroidal anti-inflammatory agent, antibiotics, anti-viral agent, lipid-soluble vitamin and the like, and combinations thereof.

The concentration of sorbic acid or a pharmaceutically acceptable salt thereof in the inventive emulsion is 0.001–5 w/v %, preferably 0.01–1 w/v %. When sodium edetate and boric acid are additionally contained, the concentration of sodium edetate is 0.001–0.2 w/v %, preferably 0.005–0.1 w/v %, and that of boric acid is 0.001–10 w/v %, preferably 0.01–5 w/v %.

While the content of the active ingredient of the inventive emulsion varies depending on the kind of drug to be contained, when the inventive emulsion contains a steroidal anti-inflammatory agent as the active ingredient, the concentration thereof is about 0.001–5 w/v %, preferably about 0.005–1 w/v %, and more preferably about 0.01–0.5 w/v %.

The oil to be contained in the inventive emulsion is preferably low toxic and less stimulating, particularly applicable to the eye, nose, ear and the like. Examples thereof include castor oil, peanut oil, cotton seed oil, soybean oil, olive oil, medium chain fatty acid triglyceride, oleic acid and the like.

The emulsion of the present invention may contain a non-ionic surfactant as an emulsifier to increase stability during emulsification. Examples of the non-ionic surfactant include polyoxyethylene sorbitan fatty acid ester (e.g. polyoxyethylene sorbitan monooleate, polyoxyethylene sorbitan monolaurate, polyoxyethylene sorbitan monopalmitate, polyoxyethylene sorbitan monostearate and the like), polyoxyethylene hydrogenated castor oil 60, sorbitan fatty acid ester (e.g. sorbitan monooleate, sorbitan monolaurate, sorbitan monopalmitate, sorbitan monostearate and the like), polyoxyethylene alkyl ether (e.g. polyoxyethylene lauryl ether and the like), polyoxyethylene fatty acid ester (e.g. polyoxyethylene monostearate and the like), and the like.

A buffering agent can be added to the emulsion of the present invention. Examples of the buffering agent include acetate such as sodium acetate, phosphate such as sodium dihydrogenphosphate, disodium hydrogenphosphate, potassium dihydrogenphosphate and dipotassium hydrogenphosphate, amino acid salt such as ε-aminocaproic acid and sodium glutamate, boric acid and a salt thereof, citric acid and a salt thereof, and the like.

The emulsion of the present invention may contain an isotonizing agent. Examples of the isotonizing agent include sodium chloride, glycerin, glucose, mannitol, sorbitol and the like.

The emulsion of the present invention may also contain various additives such as stabilizer, antioxidant, chelating agent, pH adjusting agent, thickener and the like. Examples of the antioxidant include ascorbic acid and salt thereof, tocopherol, sodium thiosulfate, sodium bisulfite, pyrvic acid and salt thereof, and the like. Examples of the chelating agent include sodium edetate, citric acid and salt thereof, and the like. The pH adjusting agent is exemplified by hydrochloric acid, phosphoric acid, acetic acid, sulfuric acid, sodium hydroxide, potassium hydroxide, sodium carbonate, sodium bicarbonate, aqueous ammonia, and the like. The pH of the inventive emulsion is preferably 2.5–8.5.

The dispersed particles of the emulsion of the present invention preferably have a median diameter of 5–0.0001 μm, more preferably 1–0.001 μm.

The emulsion of the present invention can be prepared by a known method. To be specific, sorbic acid or a pharmaceutically acceptable salt thereof, and, where necessary, sodium edetate and boric acid, and the active ingredient are dissolved in water or an aqueous solvent, if the active ingredient is water soluble. An oily phase is prepared separately (when the active ingredient is lipid-soluble, it is dissolved in this oily phase), and emulsified with the aqueous phase prepared above. As the case demands, an emulsifier and other additives can be added to the aqueous phase and/or oily phase.

More specifically, in the case of an oil in water type emulsion, for example, sorbic acid or a pharmaceutically acceptable salt thereof and, where necessary, sodium edetate and boric acid, and further, the above-mentioned additive and emulsifier are dissolved in water, and the pH thereof is adjusted to 2.5–8.5 with a pH adjusting agent. For homogeneous emulsification, a known means such as a mixer, homogenizer, microfluidizer, high pressure homogenizer and the like can be used.

Alternatively, the inventive emulsion can be prepared by the following method. That is, emulsifier and other additive are added as necessary to the inventive preservative for emulsion prepared in advance, which may comprise sorbic acid or a pharmaceutically acceptable salt thereof and, where necessary, sodium edetate and boric acid. When the active ingredient is water soluble, it is dissolved in said mixture to give an aqueous phase. Separately, emulsifier and other additive are added as necessary to an oil, and when the active ingredient is lipid soluble, it is dissolved in said oil to give an oily phase. Then, said aqueous phase and oily phase are emulsified by a known method.

The emulsion of the present invention is preferably used as an emulsion for local administration to the eye, nose or ear. More preferably, it is formulated into a dosage form for instillation to the eye, nose or ear.

The emulsion of the present invention shows high preservation property attributable to the preservative contained therein, which is capable of exerting superior preservation effect even at a low concentration, and thus, is associated with extremely less side effects caused by the preservative.

The present invention is described in more detail by way of Examples and Experimental Examples, which should not be construed as limiting the invention.

EXAMPLE 1

|  | (in 100 ml) |
| --- | --- |
| castor oil | 5.0 g |
| polysorbate 80 | 4.0 g |
| conc. glycerin | 2.6 g |
| sodium acetate | 0.01 g |
| sorbic acid | 0.1 g |
| sodium hydroxide | appropriate amount |
| sterile purified water | appropriate amount |
|  | (pH 5.0) |

The sterile purified water was heated to about 70° C., and polysorbate 80, conc. glycerin, sodium acetate and sorbic acid were added for dissolution. The pH was adjusted to 5.0 with sodium hydroxide. While stirring this solution in a homomixer, castor oil heated to about 70° C. was added to give a crude emulsion. The particles in the crude emulsion were finely divided in a microfluidizer, and the resulting emulsion is sterilized by filtration to give a fine emulsion.

EXAMPLE 2

|  | (in 100 ml) |
| --- | --- |
| retinol palmitate | 100,000 I.U. |
| castor oil | 5.0 g |
| polysorbate 80 | 4.0 g |
| conc. glycerin | 2.0 g |
| sodium acetate | 0.01 g |
| boric acid | 0.5 g |
| sorbic acid | 0.1 g |
| sodium edetate | 0.05 g |
| sodium hydroxide | appropriate amount |
| sterile purified water | appropriate amount |
|  | (pH 6.0) |

The sterile purified water was heated to about 70° C., and polysorbate 80, conc. glycerin, sodium acetate, sorbic acid, boric acid and sodium edetate were added for dissolution. The pH was adjusted to 6.0 with sodium hydroxide to give an aqueous phase mixture. Separately, castor oil was heated to about 70° C. and retinol palmitate was added and dissolved to give an oily phase. While stirring the aqueous phase mixture heated to about 70° C. in a homomixer, the oily phase heated to about 70° C. was added to give a crude emulsion. The particles in the crude emulsion were finely divided in a microfluidizer, and the resulting emulsion is sterilized by filtration to give a fine emulsion.

EXAMPLE 3

| | (in 100 ml) |
|---|---|
| tocopherol acetate | 0.01 g |
| castor oil | 5.0 g |
| polysorbate 80 | 4.0 g |
| conc. glycerin | 2.2 g |
| ε-aminocaproic acid | 0.05 g |
| sorbic acid | 0.2 g |
| hydrochloric acid | appropriate amount |
| sterile purified water | appropriate amount (pH 5.0) |

The sterile purified water was heated to about 70° C., and polysorbate 80, conc. glycerin, ε-aminocaproic acid and sorbic acid were added for dissolution. The pH was adjusted to 5.0 with hydrochloric acid to give an aqueous phase mixture. Separately, castor oil was heated to about 70° C. and tocopherol acetate was added and dissolved to give an oily phase. While stirring the aqueous phase mixture heated to about 70° C. in a homomixer, the oily phase heated to about 70° C. was added to give a crude emulsion. The particles in the crude emulsion were finely divided in a microfluidizer, and the resulting emulsion is sterilized by filtration to give a fine emulsion.

EXAMPLE 4

| | (in 100 ml) |
|---|---|
| pirenoxine | 0.005 g |
| castor oil | 5.0 g |
| polysorbate 80 | 4.0 g |
| conc. glycerin | 2.6 g |
| sodium acetate | 0.01 g |
| boric acid | 0.1 g |
| sorbic acid | 0.1 g |
| sodium edetate | 0.05 g |
| sodium hydroxide | appropriate amount |
| sterile purified water | appropriate amount (pH 3.0) |

The sterile purified water was heated to about 70° C., and polysorbate 80, conc. glycerin, sodium acetate, sorbic acid, boric acid and sodium edetate were added for dissolution. The pH was adjusted to 3.0 with sodium hydroxide to give an aqueous phase mixture. Separately, castor oil was heated to about 70° C. and pirenoxine was added and dissolved to give an oily phase. While stirring the aqueous phase mixture heated to about 70° C. in a homomixer, the oily phase heated to about 70° C. was added to give a crude emulsion. The particles in the crude emulsion were finely divided in a microfluidizer, and the resulting emulsion is sterilized by filtration to give a fine emulsion.

COMPARATIVE EXAMPLE 1

| | (in 100 ml) |
|---|---|
| castor oil | 5.0 g |
| polysorbate 80 | 4.0 g |
| conc. glycerin | 2.6 g |
| sodium acetate | 0.01 g |
| benzalkonium chloride | 0.005 g |
| hydrochloric acid | appropriate amount |
| sterile purified water | appropriate amount (pH 5.0) |

In the same manner as in Example 1 except that benzalkonium chloride was used instead of sorbic acid and the pH was adjusted with hydrochloric acid instead of sodium hydroxide, a fine emulsion having the above-mentioned formulation was obtained.

COMPARATIVE EXAMPLE 2

| | (in 100 ml) |
|---|---|
| castor oil | 5.0 g |
| polysorbate 80 | 4.0 g |
| conc. glycerin | 2.6 g |
| sodium acetate | 0.01 g |
| chlorhexidine gluconate | 0.005 g |
| hydrochloric acid | appropriate amount |
| sterile purified water | appropriate amount (pH 5.0) |

In the same manner as in Example 1 except that chlorhexidine gluconate was used instead of sorbic acid and the pH was adjusted with hydrochloric acid instead of sodium hydroxide, a fine emulsion having the above-mentioned formulation was obtained.

COMPARATIVE EXAMPLE 3

| | (in 100 ml) |
|---|---|
| castor oil | 5.0 g |
| polysorbate 80 | 4.0 g |
| conc. glycerin | 2.6 g |
| sodium acetate | 0.01 g |
| methyl p-hydroxybenzoate | 0.026 g |
| propyl p-hydroxybenzoate | 0.014 g |
| hydrochloric acid | appropriate amount |
| sterile purified water | appropriate amount (pH 5.0) |

In the same manner as in Example 1 except that methyl p-hydroxybenzoate and propyl p-hydroxybenzoate were used instead of sorbic acid and the pH was adjusted with hydrochloric acid instead of sodium hydroxide, a fine emulsion having the above-mentioned formulation was obtained.

EXPERIMENTAL EXAMPLE 1

Preservation Effect Test (1)

The preservation effect of the emulsions of the above-mentioned Example 1 and Comparative Examples 1–3 was tested according to the United States Pharmacoponia (U.S.P.) 231, <51> ANTIMICROBIAL PRESERVATIVES-EFFECTIVENESS.

The results are shown in Table 1–Table 4.

TABLE 1

Antimicrobial preservatives-effectiveness (emulsion of Example 1)

| microorganism | initial | Time (weeks) | | | |
|---|---|---|---|---|---|
| | | 1 | 2 | 3 | 4 |
| Staphylococcus aureus | 6 | n.d. | n.d. | n.d. | n.d. |
| Escherichia coli | 6 | 3 | n.d. | n.d. | n.d. |
| Pseudomonas aeruginosa | 6 | n.d. | n.d. | n.d. | n.d. |
| Candida albicans | 5 | 5 | 5 | 2 | n.d. |
| Aspergillus niger | 5 | 5 | 5 | 4 | 4 | unit: log CFU/ml
n.d.: not detected

TABLE 2

Antimicrobial preservatives-effectiveness
(emulsion of Comparative Example 1)

| microorganism | initial | Time (weeks) | | | |
|---|---|---|---|---|---|
| | | 1 | 2 | 3 | 4 |
| Staphylococcus aureus | 6 | n.d. | n.d. | n.d. | n.d. |
| Escherichia coli | 6 | 5 | 5 | 5 | 5 |
| Pseudomonas aeruginosa | 6 | 2 | n.d. | n.d. | n.d. |
| Candida albicans | 5 | 5 | 6 | 5 | 5 |
| Aspergillus niger | 5 | 4 | 5 | 5 | 4 | unit: log CFU/ml
n.d.: not detected

TABLE 3

Antimicrobial preservatives-effectiveness
(emulsion of Comparative Example 2)

| microorganism | initial | Time (weeks) | | | |
|---|---|---|---|---|---|
| | | 1 | 2 | 3 | 4 |
| Staphylococcus aureus | 6 | 1 | n.d. | n.d. | n.d. |
| Escherichia coli | 6 | 4 | 3 | 3 | 2 |
| Pseudomonas aeruginosa | 6 | n.d. | n.d. | n.d. | n.d. |
| Candida albicans | 5 | 6 | 5 | 5 | 4 |
| Aspergillus niger | 5 | 4 | 5 | 4 | 4 | unit: log CFU/ml
n.d.: not detected

TABLE 4

Antimicrobial preservatives-effectiveness
(emulsion of Comparative Example 3)

| microorganism | initial | Time (weeks) | | | |
|---|---|---|---|---|---|
| | | 1 | 2 | 3 | 4 |
| Staphylococcus aureus | 6 | 1 | n.d. | n.d. | n.d. |
| Escherichia coli | 6 | 5 | 4 | 4 | 3 |
| Pseudomonas aeruginosa | 6 | n.d. | n.d. | n.d. | n.d. |
| Candida albicans | 5 | 6 | 6 | 6 | 6 |
| Aspergillus niger | 5 | 4 | 4 | 4 | 4 | unit: log CFU/ml
n.d.: not detected

The above results reveal that bacteria were eradicated in 2 weeks only in the emulsion having the formulation of Example 1 including sorbic acid, and no proliferation of fungi was observed, thus showing superior preservation effect verified against U.S.P.

EXAMPLE 5

| | (in 100 ml) |
|---|---|
| castor oil | 5.0 g |
| polysorbate 80 | 4.0 g |
| conc. glycerin | 2.2 g |
| sodium acetate | 0.05 g |
| boric acid | 0.1 g |
| sorbic acid | 0.1 g |
| sodium edetate | 0.2 g |
| sodium hydroxide | appropriate amount |
| sterile purified water | appropriate amount (pH 6.0) |

In the same manner as in Example 1 except that sodium edetate and boric acid were added concurrently with sorbic acid, a fine emulsion having the above-mentioned formulation was obtained.

EXPERIMENTAL EXAMPLE 2

Preservation Effect Test (2)

In the same manner as in Experimental Example 1, the preservation effect was tested with respect to the emulsion having the formulation of the above-mentioned Example 5.

The results are shown in Table 5.

TABLE 5

Antimicrobial preservatives-effectiveness (emulsion of Example 5)

| microorganism | initial | Time (weeks) | | | |
|---|---|---|---|---|---|
| | | 1 | 2 | 3 | 4 |
| Staphylococcus aureus | 6 | 4 | n.d. | n.d. | n.d. |
| Escherichia coli | 6 | 6 | n.d. | n.d. | n.d. |
| Pseudomonas aeruginosa | 6 | n.d. | n.d. | n.d. | n.d. |
| Candida albicans | 5 | 5 | 5 | 5 | 5 |
| Aspergillus niger | 5 | 4 | 4 | 4 | 3 | unit: log CFU/ml
n.d.: not detected

As is evident from Table 5, bacteria were eradicated in 2 weeks in the emulsion having the formulation of Example 5 including sorbic acid, boric acid and sodium edetate and no proliferation of fungi was observed, thus showing superior preservation effect verified against U.S.P.

EXAMPLE 6

| | (in 100 ml) |
|---|---|
| medium chain fatty acid triglyceride | 5.0 g |
| polysorbate 80 | 4.0 g |
| conc. glycerin | 2.6 g |
| sodium acetate | 0.05 g |
| sorbic acid | 0.1 g |
| sodium hydroxide | appropriate amount |
| sterile purified water | appropriate amount (pH 5.0) |

In the same manner as in Example 1 except that medium chain fatty acid triglyceride was used instead of castor oil, a fine emulsion having the above-mentioned formulation was obtained.

COMPARATIVE EXAMPLE 4

| | (in 100 ml) |
|---|---|
| medium chain fatty acid triglyceride | 5.0 g |
| polysorbate 80 | 4.0 g |
| conc. glycerin | 2.6 g |
| sodium acetate | 0.05 g |
| benzalkonium chloride | 0.005 g |
| hydrochloric acid | appropriate amount |
| sterile purified water | appropriate amount (pH 5.0) |

In the same manner as in Comparative Example 1 except that medium chain fatty acid triglyceride was used instead of castor oil, a fine emulsion having the above-mentioned formulation was obtained.

EXPERIMENTAL EXAMPLE 3

Preservation Effect Test (3)

In the same manner as in Experimental Example 1, the preservation effect was tested with respect to the emulsions having the formulations of the above-mentioned Example 6 and Comparative Example 4.

The results are shown in Table 6 and Table 7.

TABLE 6

Antimicrobial preservatives-effectiveness (emulsion of Example 6)

| microorganism | initial | 1 | 2 | 3 | 4 |
|---|---|---|---|---|---|
| Staphylococcus aureus | 6 | n.d. | n.d. | n.d. | n.d. |
| Escherichia coli | 6 | n.d. | n.d. | n.d. | n.d. |
| Pseudomonas aeruginosa | 6 | n.d. | n.d. | n.d. | n.d. |
| Candida albicans | 5 | n.d. | n.d. | n.d. | n.d. |
| Aspergillus niger | 5 | 3 | 2 | 1 | n.d. | unit: log CFU/ml
n.d.: not detected

TABLE 7

Antimicrobial preservatives-effectiveness (emulsion of Comparative Example 4)

| microorganism | initial | 1 | 2 | 3 | 4 |
|---|---|---|---|---|---|
| Staphylococcus aureus | 6 | n.d. | n.d. | n.d. | n.d. |
| Escherichia coli | 6 | 6 | 4 | n.d. | n.d. |
| Pseudomonas aeruginosa | 6 | 3 | 3 | 3 | 3 |
| Candida albicans | 5 | 5 | 5 | 5 | 5 |
| Aspergillus niger | 5 | 5 | 4 | 4 | 4 | unit: log CFU/ml
n.d.: not detected

The above results reveal that bacteria were eradicated in 1 week in the emulsion having the formulation of Example 6 including sorbic acid and medium chain fatty acid triglyceride as an oil and no proliferation of fungi was observed, thus showing superior preservation effect verified against U.S.P.

This application is based on application No. 46548/1997 filed in Japan, the content of which is incorporated hereinto by reference.

What is claimed is:

1. A method for preserving an emulsion for greater than 3 weeks against fungi, consisting essentially of adding to an emulsion sorbic acid or a pharmaceutically acceptable salt thereof, sodium edetate and boric acid, at concentrations which are pharmaceutically acceptable and effective for preservation of the emulsion.

2. The method according to claim 1, wherein the pH of the emulsion is in a range of 6.0 to 8.5.

3. The method of claim 1, wherein the sodium edetate is added at a concentration of 0.001–0.2 w/v %, and the boric acid is added at a concentration of 0.001–10 w/v %.

4. The method of claim 1, wherein the sodium edetate is added at a concentration of 0.005–0.1 w/v %, and the boric acid is added at a concentration of 0.01–5 w/v %.

5. The method of claim 1, wherein the sorbic acid or a pharmaceutically acceptable salt thereof is added at a concentration of 0.01–1 w/v %, the sodium edetate is added at a concentration of 0.005–0.1 w/v %, and the boric acid is added at a concentration of 0.01–5 w/v %.

6. The method of claim 1, which is for preserving an emulsion in the dosage form of an eye drop, a nasal drop or an ear drop.

\* \* \* \* \*